United States Patent [19]

Dall'Asta et al.

[11] Patent Number: 5,621,085
[45] Date of Patent: Apr. 15, 1997

[54] PROCESS FOR THE PREPARATION OF AMIKACIN PRECURSORS

[75] Inventors: Leone Dall'Asta, Pavia; Eugenio Garegnani, Marcallo con Casone, both of Italy

[73] Assignee: Biochimica Opos S.p.A., Milan, Italy

[21] Appl. No.: 459,649

[22] Filed: Jun. 2, 1995

Related U.S. Application Data

[62] Division of Ser. No. 402,328, Mar. 10, 1995.

[30] Foreign Application Priority Data

Mar. 8, 1990 [IT] Italy ........................ 19620/90
Jul. 30, 1990 [IT] Italy ........................ 21127/90

[51] Int. Cl.$^6$ ........................................ C07H 1/00
[52] U.S. Cl. ..................... 536/13.8; 536/13.7; 536/18.5
[58] Field of Search .................... 536/13.7, 13.8, 536/18.5

[56] References Cited

U.S. PATENT DOCUMENTS

| | | | |
|---|---|---|---|
| 4,140,849 | 2/1979 | Umezawa et al. | 536/13.8 |
| 4,902,790 | 2/1990 | Mangia et al. | 536/13.7 |
| 4,985,549 | 1/1991 | Giobbio et al. | 536/13.8 |

FOREIGN PATENT DOCUMENTS

0446671A1  9/1991  European Pat. Off. .

OTHER PUBLICATIONS

Tsuchiya et al., *1–N–Acylation of Aminocyclitol Antibiotics Via Zinc Chelation and Regiospecific N–Trifluoroacetylation*, Tetrahedron Letters No. 51, pp. 4951–4954.

N.M. Alykov, *Complex Compounds of Pyrocatechol Volet with Aluminum and Aminogloycoside Antibiotics*, Astrakhan Pedagogical Institute, vol. 39, No. 8, pp. 1425–1427, 1984.

*Primary Examiner*—Elli Peselev
*Attorney, Agent, or Firm*—Nikaido, Marmelstein, Murray & Oram LLP

[57] ABSTRACT

Process for the preparation of a 3,6'-di-N-Acyl-1-[L-(–)-4-Acylamino-2-hydroxybutyryl] kanamycin A, wherein Acyl is a N-protecting acylating group, which comprises reacting kanamycin A with an aluminum salt in an inert organic solvent, treating the aluminum complex thus obtained with a N-acylating agent and acidifiying the reaction mixture, as such or after having removed the complexing aluminum in basic medium and isolated the 3,6'-di-N-Acyl-kanamycin A, to pH 6, treating the protonated 3,6'-di-N-Acyl-kanamycin A, in form of a salt thereof, with an active derivative of L-(–)-4-Acyl-amino-2-hydroxybutyric acid, wherein Acyl is a N-protecting group preferably identical with that which protects the amino groups in the positions 3 and 6' of kanamycin A, and isolating the product thus obtained by simple correction of the pH.

11 Claims, No Drawings

PROCESS FOR THE PREPARATION OF AMIKACIN PRECURSORS

This is a division, of application Ser. No. 08/402,328 filed Mar. 10, 1995.

The present invention concerns a process for the preparation of precursors of 0-3-amino-3-deoxy-α-D-glucopyranosyl-(1→6)-0-[6-amino-6-deoxy-α-D-glucopyranosyl-(1→4)]-N$^1$-(4-amino-2-hydroxy-1-oxobutyl)-2-deoxy-D-streptamine having the formula (A)

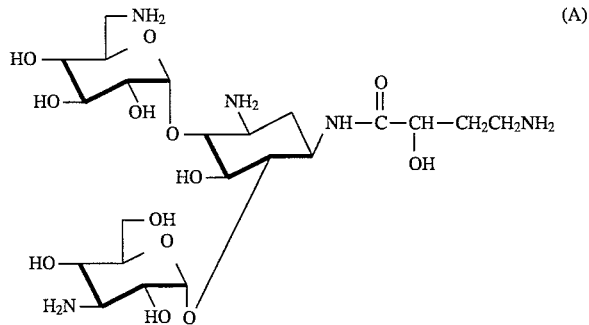

The compound of formula (A) is a semisynthetic antibiotic described in U.S. Pat. No. 3,781,268 which will be hereinafter designated by its International Non-Proprietary Name "amikacin". Amikacin is the product of acylation of the amino group in the position 1 of 0-3-amino-3-deoxy-α-D-glucopyranosyl-(1→6)-0-[6-amino-6-deoxy-α-D -glucopyranosyl-(1→4)]-2-deoxy-D-streptamine having the formula (B)

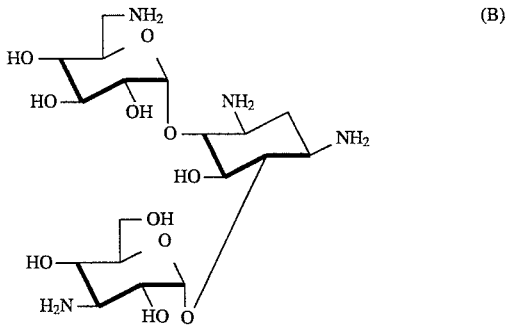

designated hereinbelow by its generic name "kanamycin A", even in the case of derivatives thereof, with L-(–)-4-amino-2-hydroxybutyric acid of formula (C)

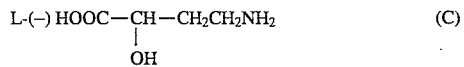

According to the above U.S. Patent, amikacin is prepared by treatment of 6'-N-monobenzyloxycarbonylkanamycin A with an active ester of L-(–)-N -benzyloxycarbonyl-4-amino-2-hydroxybutyric acid, preferably its ester with N-hydroxysuccinimide of formula (D)

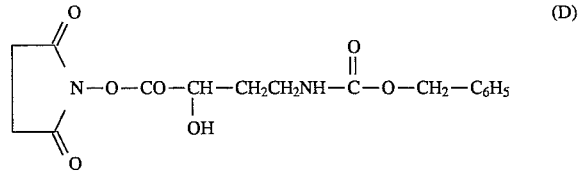

and by further hydrogenolysis of the thus obtained 1-N-[L-(–)-4-benzyl oxycarbonylamino-2-hydroxybutyryl]-6'-N-benzyloxycarbonylkanamycin A. Furthermore, other and more advantageous preparation methods for amikacin have been proposed; such methods provide the protection of the other reactive groups which are present in kanamycin A because the protection of only the 6'-NH$_2$ group disclosed in U.S. Pat. No. 3,781,268 is not sufficient to warrant the obtention of amikacin in good yields. Thus, U.S. Pat. No. 3,974,137 provides a protection of amino groups with aldehydes; U.S. Pat. No. 4,347,354 and 4,424,343 provide a protection by total silylation and partial desilylation.

U.S. Pat. No. 4,136,254 and 4,230,847 disclose the protection of the amino groups in the position 3 and 6' of kanamycin A by previous blocking of the other amino groups by complexation with a divalent transition metal selected among copper, nickel, cobalt and cadmium, introduction of a N-protecting group in both the positions 3 and 6' and removal of the complexing metal. Analogously, U.S. Pat. No. 4,297,485 discloses the same protection in both the positions 3 and 6' of kanamycin A by previous complexation with zinc, introduction of the protecting group and removal of the complexing metal.

According to these documents there is obtained a 3,6'-di-N-Acyl-kanamycin A which is converted to amikacin either by direct acylation of the 1-NH$_2$ group with the reactive derivative (D), which gives the immediate precursor of amikacin, and removal of the protecting groups (U.S. Pat. No. 4,136,254 and 4,230,847), or by previous protection of the 3"-NH$_2$ group with a trifluoroacetyl group, acylation in the position 1 and removal of the trifluoroacetyl and benzyloxycarbonyl groups (U.S. Pat. No. 4,297,485). In the first case, the presence of the free amino group in the position 3" involves undesired side reactions during the direct acylation; in the second case, the use of ethyl trifluoroacetate renders the process not very easy. European Pat. Appl. No. 218,292 discloses a process for the preparation of amikacin which comprises complexing kanamycin A, N-protected in its positions 3 and 6', with a metallic cation selected among zinc, nickel, iron, cobalt, manganese, copper, cadmium, and reacting the complex thus obtained with a reactive derivative of the N-protected acid (C). According to this document, the amount of the divalent metal salt in respect of the starting substrate can be in molar ratio varying from 1:1 to 10:1, preferably from 2:1 to 6:1, but in the specifically described process the above ratio is about 1:3.5.

One of the most important methods for the preparation of amikacin involves the use of 3,6'-di-N-Acyl-kanamycin A, preferably 3,6'-di-N-benzyloxycarbonylkanamycin A. An improved process for the preparation of these intermediates is therefore very suitable. In fact, the methods of U.S. Pat. No. 4,136,254 and 4,230,847 on one side, and of U.S. Pat. No. 4,297,485 on another side, use complexing metals which are rather polluting. Even zinc, used in U.S. Pat. No. 4,297,485, involves particular treatements in order to recuperate it.

According to U.S. Pat. No. 4,297,485, the best molar ratio kanamycin A/zinc is 1.03/4.55, but in a comparison assay 1.03 mmoles of kanamycin A and 1.24 mmoles of zinc acetate dihydrate gave a 51% yield of 3,6'-di -N-benzyloxycarbonylkanamycin A against a yield of 7.3% using nickel (II) acetate tetrahydrate (U.S. Pat. No. 4,136,254 and 4,230, 847) as a complexing agent.

It has now been found that a 3,6'-di-N-Acyl-kanamycin A can be prepared in an extremely easy manner by complexing kanamycin A with aluminum, namely with a trivalent and only trivalent metal, then di-N-acylating the amino groups in the position 3 and 6' and finally decomposing the complex.

It has also surprisingly found that the ratio substrate/aluminum salt in the formation of the complex can be 1:1 to 1:4 and that greater ratios are not necessary.

Furthermore, it has been found that the 3,6'-di-N-acylation of the complex with aluminum occurs in very high yields and that the decomposition of the complex in a basic medium does not present any difficulty, giving pure 3,6'-di-N-Acyl-kanamycin A in excellent global yields.

Moreover, it has been found that, after complexation, 3,6'-di-N-acylation and decomposition of the aluminum complex, there is obtained a very poor residue of unreacted starting kanamycin A.

In addition, it has surprisingly been found that amikacin can be prepared in an extremely easy manner by acidifying an aqueous suspension of 3,6'-di-N-protected kanamycin A, until a complete dissolution is obtained, then acylating the amino group in the position 1 and selectively deprotecting in 3,6' the triacylated precursor thus obtained.

It has further been found that the N-acylation in the position 1 of the thus protonated 3,6'-di-N-Acyl-kanamycin A takes place in very high yields and that, when the reaction is over, the precursor of amikacin is obtained in a sufficiently pure form and in excellent global yields by simple adjustment of the pH with a base.

Finally, it has been found that the whole synthesis of amikacin precursors starting from kanamycin A can be carried out without isolating the 3,6'-di-N-Acyl-kanamycin A by subjecting the aluminum complex, obtained at the end of the 3,6'-di-N-Acylation of the aluminum complex of kanamycin A, to a treatment with an acid in order to obtain a salt of 3,6'-di-N-Acyl-kanamycin A on the amino groups in the 3" and 1 positions.

This finding is surprising because the selective protection of the 3"-amino group even in the presence of a 1,3"-diprotonated product was unexpected.

Thus, in summary, the present invention relates to a process for the preparation of amikacin precursors starting from kanamycin A in which the two main steps, namely:

the preparation of 3,6'-di-N-Acyl-kanamycin A through an aluminum complex, and the 1-acylation of the 3,6'-di-N-Acyl-kanamycin A through a 3"-N-protection by protonation are novel and in which novel salts of 3,6'-di-N-Acyl-kanamycin A on the 1 and 3" amino groups are used as useful intermediates in said process. More particularly, the present invention concerns a process for the preparation of an amikacin precursor of formula (I)

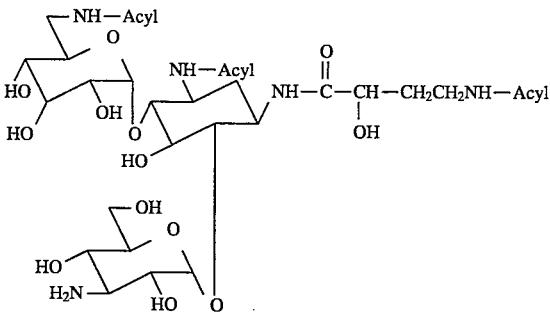

in which Acyl is an acylating N-protecting group, which comprises (a) reacting kanamycin A with an aluminum salt in an aqueous-organic medium;

(b) reacting the aluminum complex of kanamycin A thus obtained with a reactive derivatives of the acid of formula (II)

Acyl-OH    (II)

wherein Acyl is as defined above;

(c) treating the aluminum complex of the 3,6'-di-N-Acyl-kanamycin A, as such or after having decomposed it in a basic medium, with a proton donor until a pH value of about 6 is obtained;

(d) treating the protonated 3,6'-di-N-Acyl-kanamycin A thus obtained with a reactive derivative of N-protected L-(−)-4-amino-2-hydroxy butyric acid of formula (III)

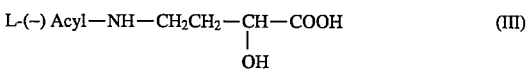

wherein Acyl is as defined above and finally isolating the 1-N-acylated product of formula (I) thus obtained.

In the step (a), the starting kanamycin A is preferably used as free base, dissolved or suspended in an inert organic solvent, preferably water-miscible. Particularly preferred organic solvents are polar aprotic compounds such as dimethyl sulfoxide, dimethylformamide or dimethylacetamide.

As aluminum salt there is used a salt of aluminum with a weak acid having a $pK_a$ in the range of from about 3 to about 5, preferably the basic acetate, advantageously in an aqueous solution freshly prepared by reaction of aluminum chloride and sodium acetate. The amount of aluminum salt used for this reaction is of at least one mole per mole of starting kanamycin A and, in this condition, good yields of final product are obtained, but the molar ratio kanamycin A/aluminum can vary from 1:1 to 1:4, preferably from 1:1.5 to 1:4, better from 1:2 to 1:3. Larger amounts of aluminum salt are not necessary. The reaction is carried out at a temperature of from about 10° C. to about 55° C., preferably at 15°–45° C. for 2–4 hours. In the step (b), the reaction mixture containing the aluminum complex of kanamycin A is treated with the reactive derivative of the acid (II). In the formula (II), Acyl is the acylating N-protecting group which has to be introduced in the 3 and 6' positions of kanamycin A. The protecting groups include the usual blocking groups for the protection of primary amino groups, well known in the art, namely Acyl groups which can be removed by mild acid hydrolysis or catalytic hydrogenation.

Particularly suitable N-protecting groups include alkoxycarbonyl groups, such as t-butoxycarbonyl and t-amyloxycarbonyl; aralkoxy carbonyl groups, such as benzyloxycarbonyl; cycloalkyloxycarbonyl groups, such as cyclohexyloxycarbonyl; haloalkoxycarbonyl groups, such as trichloroethoxycarbonyl; acyl groups, such as phtaloyl and o-nitro phenoxyacetyl.

The preferred N-protecting Acyl group is benzyloxycarbonyl.

As a reactive derivative of the acid Acyl-OH may be used anyone of the functional derivatives capable of acylating primary amines, such as the acid itself duly activated with dicyclohexylcarbodiimide or the acid chloride, its anhydride, or a mixed anhydride, an active ester such as the 4-nitrophenyl ester or, preferably, the ester with N-hydroxy succinimide. The preferred product is the N-benzyloxycarbonyloxy succinimide of formula (E)

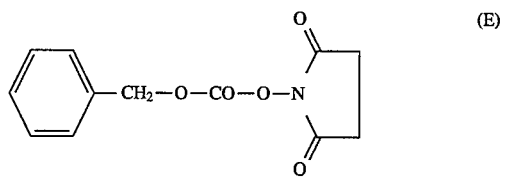

hereinafter designated "N-BCS".

The 3,6'-di-N-acylation is carried out according to the methods known in the art. Preferably the reaction is carried out in the same solvent used in the step (a). Practically, a solution of the reactive derivative of the acid (II) in the inert organic solvent used in step (a) is added to the reaction mixture obtained at the end of the step (a). After 2–4 hours at room temperature, the 3,6'-di-N-acylation is over and the aluminum complex of the 3,6'-di-N-Acyl-kanamycin A is subjected to the following step.

Thus, in the step (c), the reaction mixture may be treated with an aqueous solution of a base up to a pH comprised between 9 and 11, preferably, between 9.5 and 10.5.

There is so obtained the decomposition of the aluminum complex and a 3,6'-di-N-Acyl-kanamycin A is isolated by simple filtration. An alkaline hydroxide or carbonate or ammonium hydroxide may be used as a base.

The 3,6'-di-N-Acyl-kanamycin A thus isolated of formula (IV)

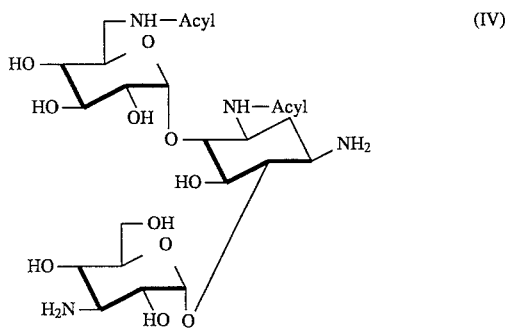

in which Acyl is as defined above, is suspended in water and the suspension thus obtained is made acid until complete dissolution.

The acid used for the above acidification is a proton donor which can be strong or weak, provided that it is added in an amount which allows the solution to reach a pH of about 6. At such a value of pH, all the starting material passes in solution, even though such a solution may appear opalescent.

As an acid, an organic proton donor may be employed, such as phenol, resorcinol or thiophenol, or a mono-, di-, or polycarboxylic acid such as formic, acetic, propionic, trimethylacetic, benzoic, salicylic, oxalic, malonic, succinic, malic, maleic, fumaric, phthalic or citric acid, a sulfonic acid such as methane- or p-toluenesulfonic acid, a phosphonic acid or a mono ($C_1$–$C_4$) alkyl ester thereof. A mineral acid may also be employed, such as hydrochloric acid, sulfuric acid or a mono ($C_1$–$C_4$) alkyl ester thereof, phosphoric acid or a mono- or di- ($C_1$–$C_4$) alkyl ester thereof, pyrophosphoric acid, boric acid. A salt of a strong acid with an organic base such as pyridine or triethylamine hydrochloride or tosylate may also be used as protonating agent. A strong acid is preferably used.

According to an advantageous embodiment, an acid is added to the aqueous suspension of compound (IV) until said compound is completely dissolved.

The acidification of the aqueous suspension of compound (IV) may be made at room temperature, preferably at 18°–25° C.

It is suitable to have the pH variation monitored during the acidification in order to stop the addition of the acid when the pH has reached the desired value.

Of course, once the operation conditions have been standardized, such a control is no longer necessary for the skilled in the art, who will use a well defined amount of acid.

The aqueous solution at pH 6 contains the diprotected kanamycin A of formula (IV) having its free amino groups in protonated form. As indicated above, the amount of the used acid is about 2 moles per mole of compound (IV).

Since the starting pH of the aqueous solution of compound (IV) must be about 6 and since it has been observed that a lower pH involves a lowering of the yields of the 1-N-acylated product, it is assumed that at such a pH the amino group in the position 3" is protonated.

Furthermore, since about 2 moles of acid are used, it is also assumed that a second protonation occurs on the amino group in the position 1, such a second protonation having no protective effect for the further 1-N-acylation reaction. This fact is surprising.

According to a preferred embodiment, when the initial acidification is made with a strong acid such as methanesulfonic acid, it is suitable to adjust the pH during the 1-N-acylation reaction in order to keep it higher than 4.

The use of a buffer solution may be useful in particular when a strong acid is employed for the initial solubilization.

When the initial acidification is made using a weak acid such as acetic acid, such a correction of pH during the 1-N-acylation reaction is no longer necessary.

When for example 3,6'-di-N-benzyloxycarbonylkanamycin A is used as starting material, the structure of the protonated compound has the formula (V)

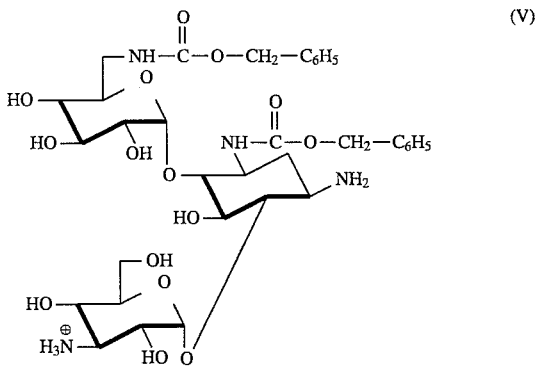

in which only the really protecting proton in 3"-position is illustrated, even if the compound is actually isolated in form of its di-salt.

The thus obtained protonated product remains in solution and such a solution is directly used for the following step.

However, a di-salt of the protonated 3,6'-di-N-Acyl-kanamycin A may be isolated and characterized.

Alternatively, step (c) may be carried out by subjecting the reaction mixture, obtained at the end of step (b) and containing the aluminum complex of the 3,6'-di-N-Acyl-kanamycin A, to the action of a proton donor as set forth above.

Thus, the protonated 3,6'-di-N-Acyl-kanamycin A is obtained without isolating the 3,6'-di-N-Acyl-kanamycin A of formula (IV).

In the step (d), the solution obtained at the end of step (c) and containing the protonated 3,6'-di-N-Acyl-kanamycin A or, alternatively, the isolated salt, is treated with a reactive derivative of the N-protected L-(−)-4-amino-2-hydroxybutyric acid, preferably with the compound having the formula (D) above.

As reactive derivative of L-(−)-4-Acylamino-2-hydroxybutyric acid may be used anyone of the functional derivatives capable of acylating primary amines, such as the acid itself duly activated with dicyclohexylcarbodiimide, or the acid chloride, its anhydride, or a mixed anhydride, an active esters such as the 4-nitrophenyl ester, or, preferably, the ester with N-hydroxysuccinimide. The preferred product is that indicated by the formula (D) above.

The reaction is carried out preferably in a water-immiscible organic solvent, preferably in methylene chloride, in 1,2-dichloroethane or in 1,1,1-trichloroethane at a temperature of from 10° to 30° C., preferably of 15°–25° C. and added to the aqueous solution of the protonated and 3,6'-di-N-protected kanamycin A; after 2–3 hours, the 3,6'-di-N-diprotected and 1-N-acylated kanamycin A is isolated from the reaction mixture according to the usual methods.

For example, the reaction mixture is treated with an aqueous solution of a base up to a pH comprised between 6.5 and 7.0, preferably 6.8. Thus, deprotonation is obtained and the final product of formula (I) is isolated by simple filtration.

An alkaline hydroxide or carbonate or ammonium hydroxide may be used as a base.

The product of formula (I) is isolated in sufficiently pure form in global yields of from 58–60% to 80% starting from 3,6'-di-N-Acyl-kanamycin A and can be converted to amikacin according to the methods known in the art by removing the acylating N-protecting groups by acid hydrolysis or hydrogenolysis. The catalytic hydrogenation of the compound of formula (I) wherein Acyl is benzyloxycarbonyl is described in U.S. Pat. No. 4,136,254 and 4,230,847.

According to the process of the present invention, the 3,6'-di-N-Acyl-kanamycin A of formula (IV) in its turn, is obtained in a very pure form and in a very satisfactory total yield starting from kanamycin A. More particularly, using a kanamycin A/aluminum ratio of 1:1, the total yield of final product is of at least 60%, namely higher than that obtained using a kanamycin A/zinc ratio of 1:1.2, described in U.S. Pat. No. 4,297,485. Moreover, yields of about 90% are obtained using a kanamycin A/aluminum ratio of 1:2, it is thus possible to have very good yields using low amounts of aluminum.

Furthermore, according to the process of the present invention, the amount of the unreacted kanamycin A recovered at the end of steps (a), (b) and of the isolation of 3,6'-di-N-Acyl-kanamycin A is very low. Normally, about 5% of kanamycin A, or even less, is recovered at the end of said steps.

Finally, according to the process of the present invention, it is possible to synthesize amikacin starting from kanamycin A even without isolating 3,6'-di-N-Acyl-kanamycin A. This feature is made possible by the preparation of a protonated 3,6'-di-N-Acyl-kanamycin A directly from the aluminum complex of said 3,6'-di-N-Acyl-kanamycin A.

Thus, the protonated 3,6'-di-N-Acyl-kanamycin A is a key intermediate in the synthesis of amikacin precursors and represents a further object of the present invention.

More particularly, the present invention also relates to a protonated 3,6'-di-N-Acyl-kanamycin A of formula (VI)

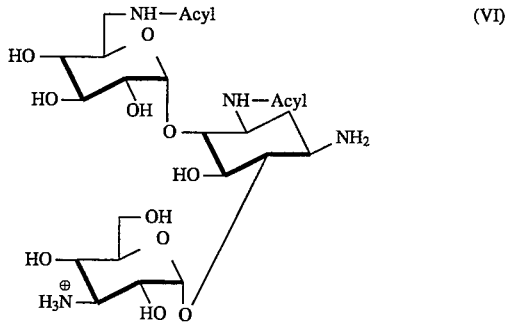

the related anion being the residue of an organic proton donor or of a mineral acid.

Preferred anions are the residues of monocarboxylic acids, more particularly the acetate and propionate anions, and the residues of sulfonic acids, more particularly the methanesulfonate (mesylate) and the p-toluenesulfonate (tosylate) anions.

The following examples illustrate the invention without, however, limiting it.

EXAMPLE 1

To a suspension of 24.2 g (50 mmoles) of kanamycin A base in 200 ml of dimethyl sulfoxide there is added a solution of 12.07 g of aluminum chloride hexahydrate (50 mmoles) and 4.1 g of anhydrous sodium acetate (50 mmoles) in 40 ml of water. After a 2-hours stirring at room temperature there is added a solution of 25 g (100 mmoles) of N-BCS in 150 ml of dimethyl sulfoxide. The mixture is stirred 3 hours at room temperature, then it is poured into ammonium hydroxide at pH 10. The precipitate is filtered and dried. There are obtained 28.3 g of 3,6'-di-N-benzyloxycarbonylkanamycin A.

EXAMPLE 2

To a suspension of 24.2 g (50 mmoles) of kanamycin A base in 200 ml of dimethylacetamide there is added a solution of 24.14 g (100 mmoles) of aluminum chloride hexahydrate and 27.20 g (200 mmoles) of sodium acetate trihydrate in 80 ml of water. The temperature rises to 45° C. After a 2-hours stirring at 40°–45° C., the temperature of the mixture is left to decrease to the room temperature. A solution of 25 g (100 mmoles) of N-BCS in 150 ml of dimethylacetamide is added to the reaction mixture and the whole is stirred 3 hours at room temperature. The mixture is poured into an aqueous solution of ammonium hydroxide at pH 10.5 and, after a 2-hours stirring at room temperature, the precipitate is filtered, washed with water and dried. There are obtained 38.2 g of 3,6'-di-N-benzyloxycarbonylkanamycin A.

EXAMPLE 3

To a suspension of 24.2 g (50 mmoles) of kanamycin A base in 200 ml of dimethyl sulfoxide there is added a solution of 48.28 g (200 mmoles) of aluminum chloride hexahydrate and 27.20 g (200 mmoles) of sodium acetate trihydrate in 160 ml of water. The temperature rises to 45° C. The reaction mixture is kept at 40°–45° C. under stirring for 2 hours. After cooling to room temperature, a solution of 25 g (100 mmoles) of N-BCS in 150 ml of dimethyl sulfoxide is added and the mixture is kept 3 hours under stirring at room temperature. Then it is poured in ammonium hydroxide at pH 10.5 and the whole mixture is stirred 2 hours at room temperature. The precipitate is filtered, washed with water and dried to give 33.1 g of 3,6'-di-N-benzyloxycarbonylkanamycin A.

EXAMPLE 4

To a suspension of 24.2 g (50 moles) of kanamycin A base in 200 ml of dimethylformamide there is added a solution of 24.14 g (100 mmoles) of aluminum chloride hexahydrate and 27.20 g (200 moles) of sodium acetate trihydrate in 80 ml of water. The temperature rises spontaneously to 45° C. The mixture is stirred 2 hours at 40°–45° C., then it is left to cool to room temperature and a solution of 25 g (100 moles) of N-BCS in 150 ml of dimethylformamide is added thereto. After 3 hours at room temperature, the reaction mixture is poured into an aqueous solution of ammonium hydroxide at pH 10.5. The mixture is stirred 2 hours at room temperature, then the precipitate is filtered, washed with water and dried. Thus, there are obtained 36.8 g of 3,6'-di-N-benzyloxycarbonylkanamycin A.

EXAMPLE 5

To a suspension in 50 ml of deionized water of 6 g of 3,6'-di-N-benzyloxycarbonylkanamycin A having purity of 85% (HPLC) there is added acetic acid at room temperature (about 20° C.) under stirring to pH 6. The solution thus obtained is cooled to 15° C., then 87.5 ml of methylene chloride containing 4.3 g of N-hydroxysuccinimide ester of L-(−)-4-benzyloxycarbonylamino-2-hydroxybutyric acid are added thereto in 30 minutes. The reaction mixture is stirred 60 minutes, whereby the temperature rises to about 18° C., while the pH decreases to 4.7. After 10–15 minutes, a thickening of the reaction mixture is observed; stirring is continued 60 minutes more, whereby the temperature rises to 20° C. A dense suspension is obtained containing a sufficiently pure 3,6'-di-N-benzyloxycarbonyl-1-N-[L-(−)-4-benzyloxycarbonylamino-2-hydroxybutyryl]kanamycin A, ready to be used as a precursor of amikacin.

EXAMPLE 6

The process is carried out exactly as described in example 5. The dense suspension obtained at the end of the acylation is concentrated to remove the solvent and the residue is taken up with 40 ml of water and treated with ammonium hydroxide to get a pH value of 6.85.

The product is filtered, washed with water and dried under vacuum at 35°–40° C. until constant weight. Thus, there are obtained 8.85 g of 3,6'-di-N-benzyloxycarbonyl-1-N-[L-(−)-4-benzyloxycarbonylamino-2-hydroxybutyryl]kanamycin A having a purity of 55.97% (HPLC). Yield: 72.2%.

EXAMPLE 7

To a suspension in 500 ml of water of 60 g of 3,6'-di-N-benzyloxycarbonylkanamycin A (purity 87.11%) there are added 8.75 ml of methane sulfonic acid to obtain a pH of 6, then the solution thus obtained is cooled to +15° C. and 860 ml of solution in methylene chloride of N-hydroxysuccinimide ester of L-(−)-4-benzyloxycarbonylamino-2-hydroxy butyric acid (obtained by reacting 37.5 g of L-(−)-4-benzyloxycarbonyl amino-2-hydroxybutyric acid with 16.25 g of N-hydroxysuccinimide in 750 ml of methylene chloride at room temperature and in the presence of 28.4 g of dicyclohexylcarbodiimide dissolved on 80 ml of methylene chloride) are added thereto in 30 minutes. By operating as described in Examples 5 and 6 there are obtained 87.7 g of 3,6'-di-N-benzyloxy carbonyl-1-N-[L-(−)-4-benzyloxycarbonylamino-2-hydroxybutyryl]kanamycin A having a purity of 46.5% (HPLC). Yield: 59.3%.

EXAMPLE 8

To a suspension in 500 ml of water of 60 g of 3,6'-di-N-benzyloxycarbonylkanamycin A (purity 87.11%) there are added 8.75 ml of methane sulfonic acid to obtain a pH of 6, then the solution thus obtained is cooled to +15° C. and 860 ml of a solution in methylene chloride of the N-hydroxysuccinimide ester of L-(−)-4-benzyloxycarbonylamino-2-hydroxytyric acid, prepared as described in Example 7, are added thereto in 30 minutes. The mixture is stirred 60 minutes, whereby the temperature rises to about 18° C. and the pH is kept between 4.5 and 5.0 by addition of ammonium hydroxide.

Stirring is continued for 60 minutes, whereby the temperature rises to 20° C. and the pH is kept in the above indicated range. A dense suspension is obtained which is concentrated under reduced pressure to remove the solvent; then the residue is taken up with 500 ml of water and the mixture is treated with ammonium hydroxide to pH 6.85. The product is filtered, washed with water and dried under vacuum at 35°–40° C. until constant weight. Thus, there are obtained 89.25 g of 3,6'-di-N-benzyloxycarbonyl-1-N-[L-(−)-4-benzyloxycarbonylamino-2-hydroxybutyryl]kanamycin A having a purity of 58.23% (HPLC). Yield: 75.7%.

EXAMPLE 9

(a) Protonated 3,6'-di-N-benzyloxycarbonylkanamycin A.

To a suspension of 6.42 g (7.6 mmoles) of 3,6'-di-N-benzyloxycarbonylkanamycin A having a titer of 89.5% (HPLC) in 50 ml of deionized water there are added 1.14 ml (15.3 mmoles) of propionic acid at 20°–22° C. to obtain a pH of 6. This solution is evaporated off under vacuum and the residue thus obtained is treated with 30 ml of isopropanol, filtered and dried under vacuum at 35° C. to give 6.5 g of 3,6'-di-N-benzyloxycarbonylkanamycin A di-propionate.

(b) 3,6'-di-N-benzyloxycarbonyl-1-N-[L-(−)-4-benzyloxycsrbonylamino-2-hydroxybutyryl]kanamycin A.

To a solution og 6.5 g of the intermediate (a), cooled to 15° C., is added in 30 minutes a solution of 4.3 g of hydroxysuccinimide ester of L-(−)-4-benzyloxycarbonylamino-2-hydroxybutyric acid in 80 ml of methylene chloride. The reaction mixture is stirred 60 minutes and a dense suspension is obtained. The product is filtered, washed with water and dried under vacuum at 35°–40° C. Thus, there is obtained 8.4 g of 3,6'-di-N-benzyloxycarbonyl-1-N-[L-(−)-4-benzyloxycarbonylamino-2-hydroxybutyryl]kanamycin A, ready to be used as a precursor of amikacin.

EXAMPLES 10–13

By operating as in the step (a) of Example 9 and substituting the appropriate proton donor for propionic acid, the following 3,6'-di-N-benzyloxycarbonylkanamycin A salts are obtained:

3,6'-di-N-benzyloxycarbonylkanamycin A diacetate (Ex. 10);

3,6'-di-N-benzyloxycarbonylkanamycin A dimethane sulfonate (Ex. 11);

3,6'-di-N-benzyloxycarbonylkanamycin A oxalate (Ex. 12);

3,6'-di-N-benzyloxycarbonylkanamycin A hydrogen citrate (Ex. 13).

EXAMPLE 14

To a suspension of 24.2 g (50 mmoles) of kanamycin A base in 200 ml of dimethyl sulfoxide there is added a solution of 24.14 g (100 mmoles) of aluminum chloride hexahydrate and 27.20 g (200 mmoles) of sodium acetate trihydrate in 80 ml of water. The temperature rises to 45° C. and the reaction mixture is kept at 40°–45° C. under stirring for 2 hours. After cooling at 18°–20° C., a solution of 25 g (100 mmoles) of N-BCS in 150 ml of dimethyl sulfoxide is added and the mixture is kept 3 hours under stirring at 18°–20° C. At this point there are in the solution the aluminum complex of the 3,6'-di-N-benzyloxycarbonylkanamycin A. After cooling at 10°–12° C., there are added 250 ml of water and successively 15 ml of propionic acid to obtain a pH of 6. The thus obtained solution contains the protonated 3,6'-di-N-benzyloxycarbonylkanamycin A. The solution is cooled to 15° C. and 547 ml of a methylene chloride solution of N-hydroxysuccinimide ester of L-(–)-4-benzyloxycarbonylamino-2-hydroxybutyric acid (obtained by reacting 23.85 g of L-(–)-4-benzyloxycarbonylamino-2-hydroxybutyric acid with 10.33 g of N-hydroxysuccinimide in 40 ml of methylene chloride at 20°–25° C. and in the presence of 18.06 g of dicyclohexylcarbodiimide) are added thereinto. The mixture is stirred for 60 minutes and the temperature rises to 18° C. Stirring is continued over 60 minutes, whereby the temperature is left to rise to 20° C. A dense suspension is obtained and concentrated to remove the methylene chloride; the residue is taken up with 110 ml of water and treated with ammonium hydroxide to a pH value of 6.85.

The product is filtered, washed with water and dried under vacuum at 35°–40° C.

Thus, there are obtained 55.78 g of 3,6'-di-N-benzyloxycarbonyl-1-N-[L-(–)-4-benzyloxycarbonylamino-2-hydroxybutyryl]kanamycin A, having a purity of 79% (HPLC), ready to be used as a precursor of amikacin.

EXAMPLE 15

Preparation of amikacin.

(i) To a solution of 25 g of 3,6'-di-N-benzyloxycarbonyl-1-N-[L-(–) -4-benzyloxycarbonylamino-2-hydroxybutyryl] kanamycin A (purity 64.5%, 16.3 mmoles) in 125 ml of aqueous acetone there are added 13.5 g. of 5% Pd/C (50% wet) and 16.5 ml of 85% formic acid. When the hydrogenolysis is over the catalyst is removed, the acetone is evaporated off and the solution is passed through a column of a slightly acid resin in its ammonium form. The fraction containing amikacin is treated with ethanol at 50° C. and the amikacin base is obtained in a 88% yield. Such a product is in accordance with the USP standard characteristics.

From the fractions containing unreacted kanamycin A, this product is recovered, as sulfate, by evaporation, treatment with 50% sulfuric acid and then with methanol.

(ii) In another preparation, the benzyloxycarbonyl groups in the 3 and 6' positions are splitted off according to the following procedure.

The above starting material (2.6 g) is dissolved in 40 ml of a mixture water/methanol 1/1 and hydrogenated for 3 hours in the presence of 0.2 g of 5% Pd/C. Then, the catalyst is removed by filtration and the filtrate is evaporated under reduced pressure. The residue thus obtained consists of amikacin in quantitative yield.

We claim:

1. A process for the preparation of an amikacin precursor having the formula (I)

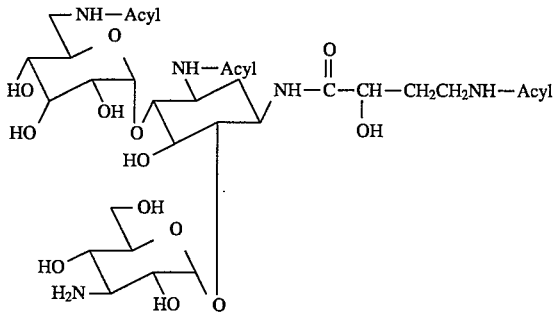

in which Acyl is an acylating N-protecting group, which comprises:

(a) reacting kanamycin A with an aluminum salt in an aqueous-organic medium;

(b) reacting the aluminum complex of kanamycin A thus obtained with a reactive derivative of an acid of formula (II)

wherein Acyl is as defined above and wherein said reactive derivative acylates primary amines, (c) treating the aluminum complex of the 3,6'-di-N-Acyl-kanamycin A thus obtained, as such or after having decomposed it in a basic medium, with a proton donor to a pH of about 6 to produce a fully protonated 3,6+-di-N-Acyl-kanamycin A;

(d) treating the solution thus obtained with a reactive derivative of a N-protected L-(–)-4-amino-2-hydroxybutyric acid of formula (III)

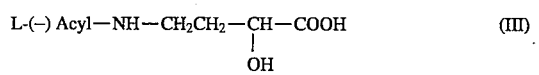

wherein Acyl has the above-stated meaning, and isolating the thus obtained 1-N-acylated product of formula (I).

2. A process according to claim 1 in which in the step (a) a salt of aluminum with a weak acid having a $pK_a$ of from about 3 to about 5 is used as an aluminum salt.

3. A process according to claim 2 in which said aluminum salt is the basic acetate.

4. A process according to claim 3 wherein basic aluminum acetate is used in form of an aqueous solution freshly prepared from aluminum chloride and sodium acetate.

5. A process according to claim 1 in which in step (a) the molar ratio kanamycin A/aluminum is of from 1:1 to 1:4.

6. A process according to claim 5 in which said ratio is of from 1:1.5 to 1:4.

7. A process according to claim 5 in which said ratio is of from 1:2 to 1:3.

8. A process according to claim 1 in which in step (b) a reactive derivative of an acid of formula Acyl-OH is used, wherein Acyl is benzyloxycarbonyl.

9. A process according to claim 1 in which in step (b) as reactive derivative of the acid of formula Acyl-OH is used its ester with N-hydroxysuccinimide.

10. A process according to claims 1, 8 or 9, in which the reactive derivative of the acid of formula Acyl-OH is the N-benzyloxycarbonyloxysuccinimide.

11. A process for the preparation of 3,6'-di-N-Acyl-kanamycin A comprising the steps of:

(a) reacting kanamycin A with aluminum salt in an aqueous-organic medium to obtain an aluminum complex of kanamycin A;

(b) reacting the aluminum complex of kanamycin A thus obtained with a reactive derivative of an acid of formula (II)

wherein Acyl is an acylating N-protecting group and wherein said reactive derivative acylates primary amines, to obtain a diacylate aluminum complex; and (c) converting the diacylate aluminum complex to obtain 3,6'-di-N-acyl kanamycin A.

* * * * *